United States Patent [19]

Auger et al.

[11] 4,190,561
[45] Feb. 26, 1980

[54] ESTERS OF CYCLOHEXENE, ODORIFEROUS COMPOSITIONS CONTAINING SAID ESTERS AND PROCESS FOR THE PREPARATION THEREOF

[75] Inventors: Bernard Auger, Peymeinade; Marcel Plattier, Antibes; Paul J. Teisseire, Grasse, all of France

[73] Assignee: Societe Anonyme Roure Bertrand Dupont, Paris, France

[21] Appl. No.: 740,361

[22] Filed: Nov. 10, 1976

[30] Foreign Application Priority Data

Nov. 17, 1975 [CH] Switzerland ............ 14896/75

[51] Int. Cl.² ............................................. C11B 9/00
[52] U.S. Cl. ........................... 252/522 R; 252/108; 252/315; 252/174.11; 424/64; 424/358; 428/350; 560/257
[58] Field of Search ............... 252/522; 260/476, 486, 260/488

[56] References Cited

U.S. PATENT DOCUMENTS 3,847,975  11/1974  Hall ............................. 252/522

FOREIGN PATENT DOCUMENTS 568721   11/1975  Switzerland ............ 252/522
572016   1/1976   Switzerland ............ 252/522
1254198  11/1971  United Kingdom ...... 252/522
1390654  4/1975   United Kingdom ...... 252/522

OTHER PUBLICATIONS

Chem. Ab. 72, 132984v, 1970, Edouard DeMole et al., Helv. Chim. Acta, 53(3), pp. 541–545, 1970.
Chem. Ab. 71, 80798v, 1969 (Kovats et al., Ger. Offen. 1,807,568).
N. P. Sopov, Chem. Ab. 63:1712d, 1965.

Primary Examiner—Veronica O'Keefe
Attorney, Agent, or Firm—Wallenstein, Spangenberg, Hattis & Strampel

[57] ABSTRACT

Novel esters of cyclohexene are disclosed having the formula

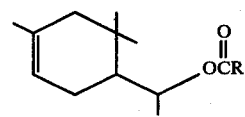

I in which R represents hydrogen or a hydrocarbon group containing from 1 to 6 carbon atoms.

These novel esters display a wide range of interesting odoriferous properties. A process for the preparation of said esters is also disclosed.

4 Claims, No Drawings

ESTERS OF CYCLOHEXENE, ODORIFEROUS COMPOSITIONS CONTAINING SAID ESTERS AND PROCESS FOR THE PREPARATION THEREOF

DETAILED DESCRIPTION OF THE INVENTION

The present invention relates to cyclohexene esters, to a process for their preparation and to odoriferous compositions containing them.

The cyclohexene esters of the invention may be represented by the general formula

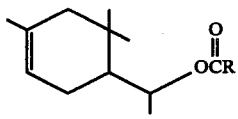   I in which R represents hydrogen or a hydrocarbon group containing from 1 to 6 carbon atoms.

The hydrocarbon group contains from 1 to 6 carbon atoms. The hydrocarbon group may be saturated or unsaturated, straight-chain or branched, and may for example be an alkyl, alkenyl, alkynyl or aryl group. Examples of compounds of the general formula I include those in which R represents hydrogen or a methyl, ethyl, propyl, secondary butyl, butyl, isobutyl, tertiary butyl, pentyl, isopentyl or hexyl; vinyl, propenyl or benzyl group.

The compounds of the invention may be prepared by any convenient process. One such process comprises esterifying an alcohol of the formula

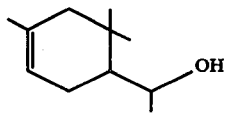   II for example, with an acid, an acid anhydride or an acid chloride.

The alcohol of the general formula II may be prepared by reducing the corresponding ketone, 1,5,5-trimethyl-4-acetyl-cyclohex-1-ene, of the formula

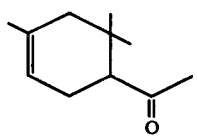   III

This latter ketone may be prepaed by a Diels-Alder condensation between isoprene and mesityl oxide. This condensation is preferably carried out in the presence of a catalyst of the Lewis acid type, such as aluminium chloride.

The compounds of formulae II and III above are novel intermediate substances and are accordingly part of the present invention.

The compounds of the general formula I have advantageous odoriferous properties. They can consequently be employed in the perfume industry for the preparation of perfumes and of perfumed products, such as soaps, liquid and solid detergents, aerosols and cosmetic products of all types, for example, toilet waters, pomades, beauty milks, face paints, lipsticks and bath salts and oils. In perfumes or perfumed products the odoriferous agents of the invention may be used in widely varying amounts: from 0.2% in detergents or toilet products up to about 10% in alcoholic perfumes. This proportion can be increased up to about 25% in perfume bases or in concentrates.

The novel odorant compounds of the general formula I according to the invention present an extensive range of odours; some have a fruity character, others floral, and others have a woody, spicy character.

The invention will now be illustrated with reference to the following Examples.

EXAMPLE 1

A 1 liter flask, provided with a mechanical stirrer, a heater and a reflux condenser fitted with a calcium chloride drying tube, is charged with 190.8 g of 1,5,5-trimethyl-4-(1-hydroxyethyl)-cyclohex-1-ene and 173.8 g of acetic anhydride. The mixture is brought to 100° for 4 hours. After cooling, the mixture is immersed in 250 ml of water and extracted with 3 times 100 ml of benzene. The extract is then washed once with 100 ml of water, twice with 100 ml of a 9% solution of sodium bicarbonate and twice more with 100 ml of water. The solvent is distilled off on a water bath, finally, under a pressure of 30 mm of mercury; the crude ester is distilled in a 500 ml three-necked flask fitted with a 1 meter adiabatic column filled with unoxidisable 4×4 mm particles, under a vacuum of 0.5 mm of mercury. 197 g of 1,5,5-trimethyl-4-(1-acetoxyethyl)-cyclohex-1-ene (81.3%) are obtained having the following physical properties:

B.p. $_{0.5}$=66°-70°

$n_D^{15}$=1.4651.

This product has a fruity odour reminiscent of the peel of hesperidites, in particular grapefruit peel.

The starting material may be prepared as follows:

(a) A flask is charged with 63 g of aluminium chloride and 2160 ml of anhydrous benzene. The apparatus is filled with nitrogen and 441 g of mesityl oxide are added, whilst stirring and maintaining the temperature of the mixture at +15°. The mixture is then left for 30 minutes at this temperature, whilst stirring. 1224 g of isoprene dissolved in 1800 ml of anhydrous benzene are then added in the course of 1 hour at +15°. Reaction is then effected for 20 hours at 16° followed by 6 hours at +25°, with stirring. The contents of the flask are then transferred to a separating funnel and the product is washed twice with 500 ml of 10% hydrochloric acid, once with 500 ml of water, once with 500 ml of a 9% solution of sodium bicarbonate and twice with 500 ml of water. The benzene is distilled off on a water bath, finally, under a pressure of 30 mm of mercury. 1070 g of crude product are obtained, which are purified in a Vigreux flask under a pressure of 1 mm of mercury. 560 g of 1,5,5-trimethyl-4-acetyl-cyclohex-1-ene (76.3%) are obtained, having the following physical properties:

B.p.$_1$=68°-69°

$n_D^{15}$=1.4718.

(b) 9.6 g of aluminium, 2.8 g of aluminium isopropylate, 0.2 g of mercuric chloride and 130 g of secondary butyl alcohol are introduced into a flask and the mixture is brought to reflux. Once the aluminium has started to react, 390 g of secondary butyl alcohol are slowly added over 45 minutes, maintaining reflux. Heating is then dicontinued and the mixture is left to attain the ambient temperature, stirring is discontinued and a calcium chloride drying tube is fitted. The mixture in then left overnight. On the following day, the mixture is brought to reflux and 332 g of 1,5,5-trimethyl-4-acetyl-cyclohex-1-ene are added in the course of about 2 hours. When the vapour temperature reaches 80°, the methyl ethyl ketone formed starts to distill off; the duration of the distillation is about 6 hours—finally under a pressure of 50 mm of mercury. The residue is taken up in 500 ml of benzene and washed twice with 100 ml of 10% sulphuric acid, twice with 100 ml of water, twice with 100 ml of a sodium bicarbonate solution and then with water until neutral. Distillation of the solvent over a water bath under reduced pressure gives 322 g of crude product, which are fractionated in a 500 ml three-necked flask fitted with a 1 meter adiabatic column having an unoxidisable filling with a particle size of 4×4 mm. 190.8 g of 1,5,5-trimethyl-4-(1-hydroxyethyl)-cyclohex-1-ene (57%) are obtained, having the following physical properties:
B.p.$_1$=63°–64°
$n_D^{15}$=1.4830.

EXAMPLE 2

20.0 g of 1,5,5-trimethyl-4-(1-hydroxyethyl)-cyclohex-1-ene are introduced into a 1 liter three-necked flask provided with a mechanical stirrer, a heater, a dropping funnel and a reflux condenser fitted with a calcium chloride drying tube. 273 g of formic acid are then added in the course of ½ hour, whilst maintaining the temperature of the reaction mixture between 0° and 5°. After the end of the addition, the temperature of the composition is maintained at 5°. The composition is then slowly heated over 2 hours to 20°–25°. The mixture is then poured into 200 ml of water and extracted with benzene. The combined benzene extracts are washed successively with water, a solution of sodium bicarbonate and, finally, with water again. After distillation of the solvent over a water bath, the crude ester is distilled under a pressure of 0.05 mm of mercury. 11.0 g of 1,5,5-trimethyl-4-(1-formyloxyethyl)-cyclohex-1-ene are obtained, having the following physical constants:
B.p.$_{0.05}$=57°
$n_D^{15}$=1.4651.
This product possesses a rich rustic odour, reminiscent of straw.

EXAMPLE 3

30.1 g of isovaleroyl chloride and 150 ml of anhydrous benzene are introduced into a 500 ml three-necked flask provided with a mechanical stirrer, a heater, a dropping funnel and a reflux condenser fitted with a calcium chloride drying tube. 33.3 g of N,N-dimethyl-aniline is then added, maintaining the temperature of the reaction composition between 10° and 15°. When the addition has ended, the composition is allowed to reach the ambient temperature and 37.8 g of 1,5,5-trimethyl-4-(1-hydroxyethyl)-cyclohex-1-ene are added over 15 minutes. The mixture is then heated to 80° for 8 hours. 56.6 g of crude isovalerate are obtained by extraction with benzene and washing as described in Example 1. On distillation under a pressure of 0.5 mm of mercury, 50.6 g of pure 1,5,5-trimethyl-4-(1-isovaleroyloxyethyl)-cyclohex-1-ene are obtained, having the following physical constants:
B.p.$_{0.5}$=103°–104°
$n_D^{17}$=1.4635.

The product has a fruity odour particularly reminiscent of apples.

EXAMPLE 4

13.55 g of α-methylbutyrol chloride and 75 ml of anhydrous benzene are introduced into a 250 ml three-necked flask provided with a stirrer, a heater, a dropping funnel and a reflux condenser fitted with a calcium chloride drying tube. 15.0 g of N,N-dimethylaniline are then added between 10° and 15°. When the addition has ended, the composition is allowed to reach the ambient temperature and 16.95 g of 1,5,5-trimethyl-4-(1-hydroxyethyl)-cyclohex-1-ene are added in the course of 15 minutes. The reaction mixture is finally heated to 70° for 2½ hours. 21.7 g of crude ester are obtained by extraction with benzene and washing as described in Example 1. By distillation under a pressure of 0.5 mm of mercury, 18.7 g pure 1,5,5-trimethyl-4-[1-(2-methylbutyroyloxy)ethyl]-cyclohex-1-ene are obtained, having the following physical constants:
B.p.$_{0.5}$=82°–86°
$n_D^{13}$=1.4650.
This product has a fruity odour related to that of wine.

EXAMPLE 5

30 g of pivaloyl chloride and 150 ml of anhydrous benzene are introduced into a 500 ml three-necked flask provided with a mechanical stirrer, a heater, a dropping funnel and a reflux condenser fitted with a calcium chloride drying tube. 33.3 g of N,N-dimethyl-aniline are then added between 10° and 15°. When the addition has ended, the composition is allowed to reach the ambient temperature and 37.8 g of 1,5,5-trimethyl-4-(1-hydroxyethyl)-cyclohexene are added in the course of 1 hour. The mixture is then heated to 50° for 2½ hours. Extraction with benzene and washing as described in example 1 yields 49.4 g of crude ester. By distillation under a pressure of 0.5 mm of mercury, 40.3 g of pure 1,5,5-trimethyl-4-(1-pivaloyloxyethyl)-cyclohex-1-ene are obtained, having the following physical constants:
B.p.$_{0.5}$=86°–91°
$n_D^{13}$=1.4620.
This product has an "agreste" (rustic or rural) odour weaker than that of the formate but more liqueur-like.

EXAMPLE 6

A three-necked flask provided with a mechanical stirrer, a heater, a dropping funnel and a reflux condenser fitted with a calcium chloride drying tube is charged with 37.1 g of enanthoyl chloride and 150 ml of anhydrous benzene. 33.3 g of N,N-dimethylaniline are then added between 10° and 15°. When the addition has ended, the composition is allowed to reach the ambient temperature and 37.8 g of 1,5,5-trimethyl-4-(1-hydroxyethyl)-cyclohexene are then added in the course of ½ hour. The mixture is then heated to 80°–87° for 13 hours. Extraction with benzene and washing as described in Example 1 yields 68 g of crude ester. By distillation under a pressure of 0.5 mm of mercury, 63,7 g of pure 1,5,5-trimethyl-4-(heptanoyloxyethyl)-cyclohex-1-ene are obtained, having the following physical constants:
B.p.$_{0.5}$=110°–112°
$n_D^{15}$=1.4674.
This compound has a flowery, lily of the valley odour, weak but with a good tenacity.

EXAMPLE 7

A 500 ml three-necked flask provided with a mechanical stirrer, a heater, a dropping funnel and a reflux condenser fitted with a calcium chloride drying tube is charged with 35.1 g of benzoyl chloride and 150 ml of anhydrous benzene. 33.3 g of N,N-dimethylaniline are then added between 10° and 15°. When the addition has ended, the composition is allowed to reach the ambient temperature and, over 15 minutes, 37,8 g of 1,5,5-trimethyl-4-(1-hydroxyethyl)-cyclohexene are added. The mixture is then heated to 20° for 8 hours. Extraction with benzene and washing as described in Example 1 yields 59.5 g of crude ester. By distillation under a pressure of 0.5 mm of mercury, 44.4 g of pure 1,5,5-trimethyl-4-(1-benzoyloxyethyl)-cyclohex-1-ene are obtained, having the following physical constants:

B.p.$_{0.5}$=123°–138°
$n_D^{17}$=1.5263.

This compound has a woody odour reminiscent of cedar and sandalwood.

EXAMPLE 8

30.1 g of crotonyl chloride and 150 ml of anhydrous benzene are introduced into a 500 ml three-necked flask provided with a mechanical stirrer, a heater, a dropping funnel and reflux condenser fitted with a calcium chloride drying tube. 33.3 g of N,N-dimethylaniline are then added over ½ an hour, whilst maintaining the temperature of the reaction mixture between 0° and 5°. When the addition has ended, the composition is allowed to reach the ambient temperature and 37.8 g of 1,5,5-trimethyl-4-(1-hydroxyethyl)-cyclohex-1-ene are added over 15 minutes. The mixture is then heated to 80° for 8 hours. 44.2 g of crude ester are obtained by extracting with benzene and washing as described in Example 1. On distillation under a pressure of 0.5 mm of mercury, 39.8 g of pure 1,5,5-trimethyl-4-(1-crotonyloxyethyl)-cyclohex-1-ene are obtained, having the following physical constants:

B.p.$_{0.5}$=102°–104°
$n_D^{15}$=1.4840.

This compound has a spicy and aromatic odour with a pronounced celery note.

EXAMPLE 9

| CHYPRE Composition | |
|---|---|
| Lemon Oil "Extra" | 7.50 g |
| Oakmoss Absolute (Tyrol) | 4.50 g |
| Coumarin | 0.90 g |
| Hibiscolide | 4.50 g |
| Styrax Resinoid No. 1 | 3.00 g |
| Linalol | 1.20 g |
| Linalyl acetate | 6.00 g |
| Bergamot Oil | 12.00 g |
| Methylionantheme gamma | 1.80 g |
| Eugenol | 1.50 g |
| Ylang-Ylang Nossi-Be No. 1 | 1.50 g |
| Patchouli Oil | 1.50 g |
| Jasmin ether | 1.50 g |
| Siam Wood Oil No. 1 Syrupy | 6.00 g |
| Ethyl phthalate | 0.60 g |
| 1,5,5-trimethyl-4-(1-acetoxyethyl)-cyclohex-1-ene | 18.00 g |
| | 72.00 g |

EXAMPLE 10

| CHYPRE Composition | |
|---|---|
| Oakmoss Absolute Oil (Tyrol) | 1.125 g |
| Coumarin | 0.225 g |
| Hibiscolide | 1.125 g |
| Styrax Resinoid No. 1 | 0.750 g |
| Linalol | 0.300 g |
| Methylionantheme gamma | 0.450 g |
| Eugenol | 0.375 g |
| Ylang-Ylang Nossi-Be No. 1 | 0.375 g |
| Patchouli Oil | 0.375 g |
| Jasmin Oil absolute, (10% in ethyl phthalate) | 0.375 g |
| Siam Wood Oil No. 1 Syrupy | 1.500 g |
| Linalyl acetate | 0.625 g |
| Lemol Peel Oil (pure) | 0.625 g |
| California Orange Oil | 0.625 g |
| Ethyl phthalate | 0.525 g |
| 1,5,5-trimethyl-4-(1-formyloxyethyl)-1-cyclohex-1-ene | 0.625 g |
| | 10.000 g |

EXAMPLE 11

| FOUGERE Composition | |
|---|---|
| Lavender Oil 40% | 20.00 g |
| Coumarin | 20.00 g |
| Patchouli Oil | 20.00 g |
| Vetiver Bourbon Oil | 10.00 g |
| Heliotropine | 10.00 g |
| Vanilla (10% in ethyl phthalate) | 20.00 g |
| Amyl salicylate | 40.00 g |
| Oakmoss Resin No. 1 (50% in ethyl phthalate) | 40.00 g |
| Ambrette Seed Oil | 10.00 g |
| Geranium Bourbon Oil | 10.00 g |
| Siam Wood Oil No 1 Syrupy 50% | 40.00 g |
| Ethyl phthalate | 32.00 g |
| 1,5,5-trimethyl-4-(1-benzoyloxyethyl)-cyclohex-1-ene | 48.00 g |
| | 320.00 g |

EXAMPLE 12

| FOUGERE Composition | |
|---|---|
| Lavender Oil 40% | 67 g |
| Coumarin | 67 g |
| Patchouli Oil | 67 g |
| Essence vetiver bourbon | 34 g |
| Heliotropine | 34 g |
| Ethyl vanilline 10% (ethyl phthalate) | 67 g |
| Amyl salicylate | 132 g |
| Oakmoss resin No. 1 (50% in ethyl phthalate) | 132 g |
| Musk ketone | 34 g |
| Geranium Bourbon Oil | 34 g |
| Siam Wood Oil No. 1 Syrupy (50% in ethyl phthalate) | 132 g |
| Ethyl phthalate | 40 g |
| 1,5,5-trimethyl-4-(1-formyloxyethyl)-cyclohex-1-ene | 160 g |
| | 1000 g |

EXAMPLE 13

| Hesperidite Composition | |
|---|---|
| 1,5,5-trimethyl-4-(1-acetoxyethyl)-cyclohex-1-ene | 2.40 g |
| Linalyl acetate | 1.60 g |

| -continued | |
|---|---|
| Hesperidite Composition | |
| Styrallyl acetate | 0.10 g |
| Lemon Oil | 0.90 g |
| | 5.00 g |

EXAMPLE 14

0.5% of the composition of Example 10 is incorporated into a liquid shampoo composed of 400 parts of sodium lauryl ether sulphate, 160 parts of triethanolamine lauryl ether sulphate, 40 parts of coconut oil acid diethanolamide, 2 parts of sodium methyl parahydroxybenzoate and 398 parts of water. The mixture has a chypre, woody odour which is particulary hesperidite in character.

EXAMPLE 15

0.2% of the ester of Example 3 is incorporated into a liquid detergent composed of 180 parts of sodium dodecylbenzenesulphonate, 300 parts of sodium lauryl ether sulphate, 80 parts of sodium xylenesulphonate and 140 parts of water. The resulting detergent has a rich fruity odour particularly reminiscent of apples.

What is claimed:
1. The compound 1,5,5-trimethyl-4-(1-formyloxy-ethyl)-cyclohex-1-ene.
2. The compound 1,5,5-trimethyl-4-(1-acetoxy-ethyl)-cyclohex-1-ene.
3. Perfume compositions containing a compound selected from the group consisting of 1,5,5-trimethyl-4-(1-formyloxy-ethyl)-cyclohex-1-ene and 1,5,5-trimethyl-4-(1-acetoxy-ethyl)-cyclohex-1-ene, said compound being present in effective amounts up to about 25%, by weight, of said perfume compositions, with additional perfume components.
4. Perfume compositions according to claim 3, in which said compounds are present in amounts from about 10% up to about 25%.

* * * * *